(12) United States Patent
Schull et al.

(10) Patent No.: US 6,307,098 B1
(45) Date of Patent: Oct. 23, 2001

(54) WATER SOLUBLE PHOSPHINES

(75) Inventors: Terrence L. Schull, Alexandria, VA (US); Walter J. Dressick, Ft. Washington, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/590,137

(22) Filed: Jun. 9, 2000

(51) Int. Cl.$^7$ .................................................. C07F 9/22
(52) U.S. Cl. ................................. 562/20; 562/8; 558/70; 564/15
(58) Field of Search ........................... 562/8, 20; 564/12, 564/15; 558/70

(56) References Cited

FOREIGN PATENT DOCUMENTS 198 24 361-A1 * 2/1999 (DE).

* cited by examiner

*Primary Examiner*—Jean F. Vollano
(74) *Attorney, Agent, or Firm*—John J. Karasek; George A. Kap

(57) ABSTRACT

This invention relates to water soluble phosphines of the following structural formula and method of preparing these phosphines:

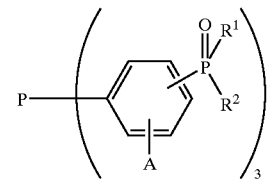

Wherein A is a moiety which is stable to the reaction conditions and does not interfere with solubility of the compound in the preparation reaction. $R^1$ and $R^2$ are selected from hydroxyl groups, dialkylamino group, and alkoxide groups.

19 Claims, No Drawings

WATER SOLUBLE PHOSPHINES

BACKGROUND OF THE INVENTION

1. Field of the Invention

This invention pertains to water soluble phosphines and process for their preparation.

2. Description of the Related Art

There has been considerable interest in aqueous and biphasic homogeneous transition metal catalysis as a means to both lower process costs and minimize adverse health and environmental concerns during manufacture. The most frequently used ligands in the metal complexes used for these reactions are functionalized triarylphosphines. Triarylphosphines are sufficiently good σ-donors and π-acceptors to stabilize synthetically useful transition metal species, yet, compared to alkylphosphines, are relatively resistant to oxidation by adventitious oxygen. This is an important factor for aqueous catalytic reactions because it is often difficult to completely remove oxygen from aqueous media.

A wide variety of cationic, anionic and non-ionic hydrophilic functional groups have been utilized to impart water solubility to triarylphosphines. Sulfonated phosphine ligands such as $P(3-C_6H_4SO_3Na)_3$ (triphenylphosphine trisulfonate, TPPTS) were demonstrated to be effective in the biphasic hydroformylation reaction commercialized by Rhone-Poulenc in the mid-1970s, and remain the most common. However, groups other than sulfonate are increasingly being investigated to extend the desirable properties of these ligands. In particular, anionic phosphonate groups and their corresponding salts are also capable of imparting a high degree of water-solubility to triarylphosphine ligands. Such groups offer a further advantage in being an excellent functionality for the synthesis of hybrid inorganic-organometallic materials. Specifically, compounds containing phosphonate groups have found broad application in the molecular fabrication of supported catalysts, chemical sensors, electroluminescent materials, and non-linear optical materials.

Known is the synthesis of $4-Ph_2PC_6H_4PO_3Na_2$ (triphenylphosphine monophosphonate disodium salt, TPPMP) from $4-Ph_2PC_6H_4Br$. Metal-halogen exchange with n-butyllithium followed by subsequent reaction of the aryllithium species with diethyl chlorophosphate gave the intermediate phosphonate ester $4-Ph_2PC_6H_4PO_3Et_2$. Transesterification with $BrSiMe_3$ followed by hydrolysis and neutralization with NaOH gave the desired compound. The phosphonate ester has also been prepared by the Pd-catalyzed reaction of $4-PPh_2C_6H_4Br$ and diethyl phosphite. In our hands, neither of these strategies was satisfactory for the preparation of the corresponding tris-phosphonate compounds, as they gave mixtures of products that were difficult to purify.

Nucleophilic aromatic substitution of fluoro arylsulfonates by phosphine or primary or secondary phosphines in the super basic medium KOH/DMSO has been shown to be a flexible and efficient route to secondary and tertiary phosphines with sulfonated aromatic substituents. Similarly, it has been reported that the triphenylphosphine diphosphonates $PhP[4-C_6H_4PO_3Na_2]_2$ and $PhP[3-C_6H_4PO_3Na_2]_2$ could be prepared by nucleophilic aromatic substitution of $4-FC_6H_4P(O)(NMe_2)_2$ or $3-FC_6H_4P(O)(NMe_2)_2$ by $PhPLi_2$, followed by acid resulting arylphosphine-phosphonodiamide, and neutralization of the free phosphonic acid with NaOH. From these reports, it was reasonable to assume that tris(4-phosphonophenyl) phosphine and its corresponding alkali metal salts could be prepared from nucleophilic aromatic substitution of the appropriate aryl fluoride by $PH_3$. We were dissuaded, however, by the toxic and pyrophoric properties of phosphine gas.

It is known that phosphide anions can be generated directly from red phosphorus by the action of alkali metals in liquid ammonia. Reduction is believed to proceed via a diphosphide anion $[P—P]^{4-}$, which, in the absence of a proton source more acidic than ammonia, is resistant to further reduction. Addition of alkyl halides gives tetraalkyldiphosphines, $R_2P-PR_2$, along with small amounts of $R_3P$. Whenever the reduction is carried out by the slow addition of one molar equivalent of a proton source such as tertiary-butyl alcohol (t-BuOH) to a 1:3 molar mixture of red phosphorus and lithium, fission of the P—P bond of the intermediate diphosphide is greatly facilitated. Subsequent addition of two equivalents of RX in Scheme 1 gives dialkylphosphines $R_2PH$ in good yield:

Scheme 1

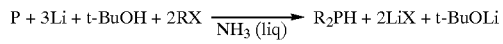

The generation of trialkyl phosphines (i.e., $R_3P$) via the use of excess RX in Scheme 1 is hindered by the decreased acidity of $R_2PH$ relative to that of $PH_3$ or $RPH_2$, which limits formation of the requisite $R_2P$ anion in amounts sufficient to yield $R_3P$ as the major reaction product. In contrast, the acidity of aromatic phosphines of the form $Ar_xPH_{(3-x)}$ (where Ar is a phenyl or substituted phenyl group and x=0, 1, 2) increases with the number of Ar groups (i.e., x). We therefore hypothesized that the progressive aryl substitution of phosphide anions to form $ArPH_2$ and $Ar_2PH$ would result in phosphine hydrides that, if present, would likely undergo deprotonation in the presence of more basic species such as $LiPH_2$ or $LiNH_2$. The resultant anions would then further react with the aryl fluoride precursors to form the desired $Ar_3P$ product.

OBJECTS AND BRIEF SUMMARY OF THE INVENTION

An object of this invention is a process for preparation of water-soluble triphenyl phosphines possessing acid derivatives as substituents on each of the phenyl rings.

Another object of this invention is the use of elemental phosphorus as a starting material for the preparation of the triphenylphosphine of this invention instead of the toxic and pyrophoric phosphine gas.

Another object of this invention is the preparation of novel water-soluble phosphines of this invention containing phosphonodiamide, phosphonic acids or phosphonate esters.

These and other objects of this invention are attained by the water-soluble triphenylphosphine having phosphonic acid groups or their derivatives on each phenyl ring made in a single pot reaction of red phosphorus, an alkali metal such as lithium, and a proton donor such as t-butanol, in liquid solvent such as liquid ammonia with an appropriate fluorophenyl phosphonic acid derivative.

DETAILED DESCRIPTION OF THE INVENTION

This invention pertains to product and process. The product is a water-soluble substituted triarylphosphine having phosphonic acid groups or its derivatives on each of the phenyl rings. The process is characterized by a single pot reaction of red phosphorus, an alkali metal such as lithium, and a proton donor (PD) such as t-butanol, in a solvent such as liquid ammonia, with an appropriate fluorophenyl phosphonic acid ester or N,N-dialkyl amide derivative.

The general reaction is depicted as follows:

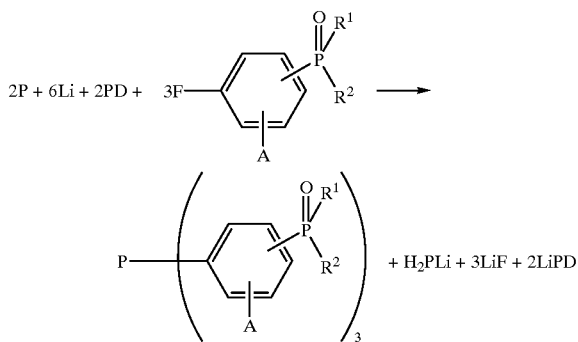

where $R^1$ and $R^2$ are same or different and are selected from dialkylamino groups containing 1–22, preferably 1–6 carbon atoms; alkoxide groups containing 1–22, preferably 1–6 carbon atoms; A, of which more than one can be present, is a substituent group(s) at positions other than the position of the phosphonate group —P(=O)($R^1$)($R^2$) and can be any organofunctional group which is stable to the reaction conditions and which maintains or does not interfere with solubility of the precursor, such as lower alkyl groups, phenyl, ether, phenol salts, dialkylamines and phenylalkyl groups; and the phosphonate group is on the phenyl ring at positions 2, 3 or 4, particularly positions 3 or 4. Another alkali metal can be used in place of lithium. Suitable alkali metals include sodium and potassium.

The structures of the compounds of this invention are shown below in Scheme 2, together with a Ronman number al designations for each compound in boldface Arc to facilitate discussion of the invention, with the phosphonate group being at position 4:

Scheme 2

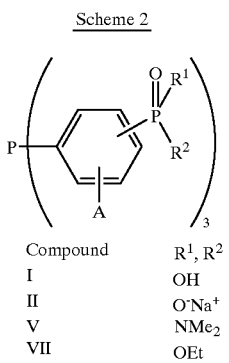

| Compound | $R^1, R^2$ |
|---|---|
| I | OH |
| II | O⁻Na⁺ |
| V | NMe$_2$ |
| VII | OEt |

The following standard abbreviations are used in Scheme 2 and throughout the description of the invention: $CH_3$=Me; $C_2H_5$=Et; $C_4H_9$=Bu. The name of each compound is given in the text at the point where the compound is first discussed.

Given the hypothesis presented in connection with Scheme 1 concerning acidities of alkyl vs. aryl phosphines, initially envisioned was a synthesis of tris(4-phosphonophenyl)phosphine, I (or the tris(4-phosphonophenyl)phosphine hexasodium salt, II), by first reacting a 1:3:1 molar ratio of P: Li: t-BuOH in mixed liquid ammonia-tetrahydrofuran (THF) solution with two mole equivalents of N,N,N',N'-tetramethyl-(4-fluorophenyl) phosphonodiamide, III, to give the secondary phosphine bis-[4-(N,N,N',N'-tetramethyl phosphonodiamide)phenyl] phosphine, IV. In situ treatment of this intermediate with n-BuLi, followed by an additional equivalent of III was expected to yield tertiary phosphine tris-[4-(N,N,N',N'-tetramethyl phosphonodiamide)phenyl]phosphine, V, as shown in Scheme 3:

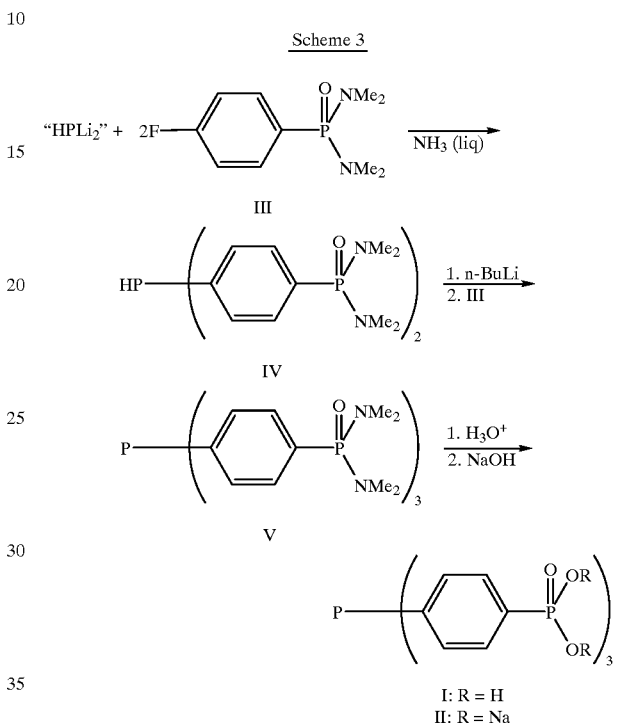

Subsequent acid hydrolysis of V, followed by neutralization with alkali, would be expected to yield II directly. Completion of the first step of this reaction sequence gave a deep red solution, which was initially believed to be the lithium salt of IV. However, analysis of the reaction mixture by $^{31}$P NMR showed little or no formation of secondary phosphine IV, or the corresponding lithium salt. Instead, the desired intermediate tertiary phosphine V was observed in low yields (i.e., <15%). Also present was unreacted III, which was identified by $^{31}$P and $^{19}$F NMR spectroscopy.

The yield of V could be optimized by using a 2:3 molar ratio of P: III. When the reaction was repeated using this stoichiometry, aryl fluoride III was completely consumed, with phosphine V being formed predominantly as shown in Scheme 4:

Scheme 4

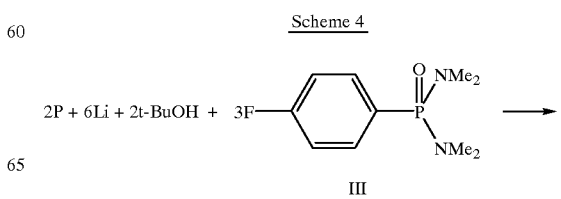

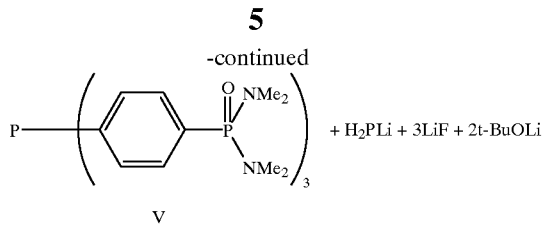

Reactions analogous to that illustrated in Scheme 4 were attempted using the O,O'-diethyl-4-fluorophenyl phosphonate, VI to synthesize tris-[4-(O,O'-dimethylphosphono)phenyl]phosphine, VII, as an alternative intermediate for hydrolysis to 1 (or II) and for the direct synthesis of II from disodium 4-fluorophenyl phosphonate, VIII. Compound VII was produced as the minor reaction product (~3%) using VI in place of III in Scheme 4. In this case, the major isolated product (~19%) was instead the monodealkylated ester, O-ethyl, O'-hydrogen-4-fluorophenyl phosphonate, IX, which was identified by $^{31}$P, $^{19}$F, and $^1$H NMR spectroscopy. Use of VIII as a starting material in Scheme 4 gave no reaction, presumably due to its poor solubility under the reaction conditions. The bulk of the starting material was recovered unchanged from the reaction mixture.

Compound I was readily prepared from V by hydrolysis under nitrogen atmosphere in boiling 2.5 M HCl (aq) solution for about 1 hour, followed by lyophilization to isolate the product as a white solid material. Attempts to perform the hydrolysis under ambient atmosphere led to partial oxidation of the phosphine site and contamination of I. Compound II was readily prepared by neutralization of I using a stoichiometric amount of NaOH (aq) solution and was purified by recrystallization from water/ethanol. Compound II was obtained as a white, efflorescent, crystalline solid with a solubility of about 550 mg/mL in water.

Having described the invention, the following examples are given to illustrate specific applications of the invention, including the best mode(s) now known to perform the invention. These specific examples are not intended to limit the scope of the invention described in this disclosure.

EXAMPLES

General. Reactions were conducted under dry, pre-purified nitrogen from liquid nitrogen boil-off using standard Schlenk line techniques when appropriate. IR spectra were recorded on a Nicolet Impact 400D FT-IR. NMR spectra were recorded on a Bruker Avance 400 spectrometer and referenced to internal TMS or 2,2,3,3,-d$_4$-3-trimethylsilylpropionic acid (TSP) for $^1$H spectra, TSP or solvent for $^{13}$C spectra, external H$_3$PO$_4$ for $^{31}$P spectra, and external benzotrifluoride for $^9$F spectra. Mass spectra were acquired using an electro-spray ionization mass spectrometer (ESMS). Flash chromatography was performed using silica gel (70–230 mesh, 60 Å pore size) under nitrogen pressure. Thin layer chromatography was done on silica gel plates with fluorescent indicator. Components were visualized with UV light or 5% ethanolic phosphomolybdate. The following materials were used as received from Aldrich Chemical Co. (values in parentheses denote purity and condition): red phosphorus (99%), lithium (99.9%), tert-butanol (99.5%, anhydrous), tetrahydrofuran (99.9%, anhydrous), methanol (99.8+%), chloroform (99+%, anhydrous), ether (99+%, anhydrous), hexane (95+%), sodium hydroxide (99.99%, electronics grade), n-butyllithium (2.5M in hexanes), 1-bromo-4-fluorobenzene (99%), diethyl chlorophosphate (97%), and silica gel (70–230 mesh, 60 angstrom pore size. N,N,N',N'-tetramethyl phosphonodiamidic chloride (Fluka, >95%) and liquid ammonia (Matheson, 99.99%, anhydrous) were used without further purification. All other materials were A.C.S. reagent grade or better and were used as received.

Example 1

Preparation of N,N,N',N'-tetramethyl-(4-fluorophenyl)phosphonodiamide, (III).

A 500-mL two-neck roundbottom flask was equipped with a magnetic stirring bar and a pressure-equalizing addition funnel. The apparatus was flushed with nitrogen and charged with n-butyllithium (69 mL of a 2.5M solution in hexanes, 0.17 mol). The solution was cooled to −78 ° C. in a dry-ice/acetone bath and a solution of 1-bromo-4-fluorobenzene (19.7 mL, 0.173 mol) in TBF (100 mL) was added dropwise with stirring. The resulting light-yellow suspension was then added slowly via cannula to a stirred solution of N,N,N',N'-tetramethyl phosphonodiamidic chloride (25 mL, 0.17 mol) in THF (150 mL) at −78° C. Once the addition was complete, the cooling bath was removed and the reaction mixture was allowed to warm to room temperature. The solvent was removed using a rotary evaporator, and the residue was taken up in dichloromethane and washed with water. The organic phase was dried over MgSO$_4$, filtered and concentrated by rotary evaporator to give a light-yellow oil. The crude product was vacuum distilled, collecting the fraction at bp 104–106° C. (0.2 mm Hg) to give 21.25 g of product (54% yield). $^{31}$P{$^1$H} NMR (CDCl$_3$): δ 29.3 (s); $^{19}$F{$^1$H} NMR (CDCl$_3$): δ-108.6 (s); $^1$H NMR (CDCl$_3$): d 7.76 (m, 2H, C$_6$H$_4$), 7.14 (m, 2H, C$_6$H$_4$), 2.64 (d, J$_{HP}$=10.1 Hz, 12H, PNMe$_2$).

Example 2

Preparation of Tris[4-(N,N,N',N'-tetramethyl phosphonodiamide)phenyl]-phosphine, (V).

A 200-mL three-neck round-bottom flask was equipped with a magnetic stirring bar, a pressure-equalizing addition funnel, and a Dewar condenser. The apparatus was flushed with nitrogen and then charged with liquid ammonia (ca. 100 mL). Red phosphorus (0.469 g, 15.1 mmol) was introduced followed by lithium metal (0.315 g, ~45.4 mmol). To the deep blue mixture was added dropwise a solution of tert-butanol (1.122 g, 15.14 mmol) in THF (20 mL) over the course of one hour. A yellow-orange suspension resulted, to which a solution of III (5.222 g, 22.70 mmol) in THF (20 mL) was added dropwise over several minutes. Within 30 minutes after the addition of the aryl fluoride, the solution had become deep red in color. The reaction mixture was stirred overnight at room temperature, allowing the ammonia to evaporate. The brick-red suspension was filtered under nitrogen, and the filtrate was concentrated under oil-pump vacuum to give a sticky yellow foam. Trituration with ether-hexane gave yellow-tinged powder, which was dried under oil-pump vacuum. The 5.08 g of product obtained is sufficiently pure to be used directly for hydrolysis to the acid, or may be further purified by chromatography on silica gel using CHCl$_3$ as the eluant, followed by 2% MeOH—CHCl$_3$, and collecting the component at R$_f$ 0.40 (10% MeOH—CHCl$_3$). $^{31}$P{ 1H} NMR (CDCl$_3$): δ 27.9 (s, PO), −4.8 (s, P); $^1$H NMR (CDCl$_3$): d 7.73 (m, 6H, C$_6$H$_4$), 7.36 (m, 6H,C$_6$H$_4$), 2.65 (d, J$_{HP}$=10.0 Hz, 18H, PNMe$_2$).

Example 3

Preparation of O,O'-diethyl-4-fluorophenyl phosphonate, (VI).

A 500-mL two-neck roundbottom flask was equipped with a magnetic stirring bar and a pressure-equalizing addition funnel. The apparatus was then flushed with nitrogen and charged with n-butyllithium (40 mL of a 2.5M solution in hexanes, 0.10 mol). The solution was cooled to −78° C. in a dry-ice/acetone bath and a solution of 1-bromo-4-fluorobenzene (11.0 mL, ~0.098 mol) in THF (80 mL) was added dropwise with stirring. The resulting white suspension (in light yellow solution) was then added slowly via cannula to a stirred solution of diethyl chlorophosphate (14 mL, ~0.097 mol) in THF (75 mL) at −78° C. A clear orange-yellow solution resulted. Once the addition was complete, the cooling bath was removed and the reaction mixture was allowed to warm to room temperature. Ether (~150 mL) was added to the reaction flask and the mixture extracted with two 175 mL portions of water. The organic phase was dried over $MgSO_4$, filtered and concentrated by rotary evaporator. The crude product was vacuum distilled, collecting the fraction at bp 88–91° C. (0.025 mm Hg) to give 12.16 g of pure VI (52% yield). $^{31}P\{^1H\}$ ($CDCl_3$)δ 18.6 (s, PO), −4.1 (s, P); $^{13}C\{^1H\}$ NMR ($CDCl_3$): δ 140.6 (dd, $J_{CP}$=16.1, 3.1 Hz), 133.3 (dd, $J_{CP}$=19.9, 19.5 Hz), 131.5 (dd, $J_{CP}$=10.4, 9.5 Hz), 129.3 (d, $J_{CP}$=188.8 Hz), 62.0 (d, $J_{CP}$=16.1 (d, $J_{CP}$=5.8 Hz); $^1H$ NMR ($CDCl_3$): δ 7.81 (m, 6H, $C_6H_4$), 7.40 (m, 6H, $C_6H_4$), 4.16 (m, 12H, $OCH_2$), 1.35 (m, 18H, $CH_3$); IR (neat film), $cm^{-1}$: 2986 (s), 2935 (m), 2909 (m), 1560 (s), 1479 (m), 1447 (m), 1405 (s), 1257 (vs), 1172 (s), 1140 (s), 1040 (vs, broad), 965 (vs, broad), 807 (s, broad), 743 (s); ESMS (positive ion mode): 671.1 $[M+H]^+$(100%).

Example 4

Preparation of O-ethyl, O'hydrogen-4-fluorophenyl phosphonate, (IX).

The procedure of example 2 was used with VI as the substrate. Red phosphorus (0.123 g, ~3.97 mol) and lithium (0.083 g, ~12.0 mmol) was stirred in liquid $NH_3$ (50 mL) and treated with a solution of t-BuOH (0.19 mL, 2.00 mmol) in THF (5 mL). A solution of VI (1.392 g, 6.000 mmol) in THF (15 mL) was then added dropwise. After overnight stirring of the reaction mixture, the reddish-brown solution was worked up by addition of 20% aqueous $NH_4Cl$ (30 mL) and ether (50 mL). The phases were separated, and the aqueous phase was extracted with an additional portion of ether. The combined ether phases were dried over $MgSO_4$, concentrated by rotary evaporator, and then oil-pump vacuum to give 0.630 g of crude product. This was chromatographed on a column (20 mm) of silica gel (40 g) using 4% $MeOH-Et_2O$ as the eluant. The first component, $R_f$ 0.51 (8% $MeOH-Et_2O$), was collected to give 0.200 g of a white solid (19% yield). This crystallized from hexane-acetone as white needles. The compound was identified as IX from $^{31}P$, $^{19}F$, $^{13}C$, and $^1H$ NMR. $^{31}P\{^1H\}$ NMR ($CDCl_3$): δ 22.2 (s, PO); $^{13}C\{^1H\}$ NMR ($CDCl_3$): δ 164.9 (dd, $J_{CF}$=252.9, $J_{CP}$=3.1 Hz), 133.6 (dd, J=11.3, 11.4 Hz), 128.0 (d, $J_{CP}$=10.4, 9.5 Hz), 129.3 (d, $J_{CP}$=77.3 Hz), 115.5 (dd, J=15.7, 15.7 Hz), 60.7 (d, $J_{CP}$=5.6 Hz), 16.3 (d, $J_{CP}$=6.4 Hz); $^1H$ NMR ($CDCl_3$): δ 7.82 (m, 2H, $C_6H_4$), 7.11 (m, 2H, $C_6H_4$), 4.06 (m, 2H, $OCH_2$), 1.31 (m, 3H, $CH_3$).

Example 5

Preparation of Tris[4-(O,O'-dimethylphosphono)phenyl]phosphine, (VII).

The chromatography of the reaction mixture from example 4 was continued after the separation of the monoester product, IX, using 8% $MeOH-Et_2O$ to elute pure VII as the second column component with $R_f$ 0.17. It was isolated as 0.112 g (3% yield) of a clear, slightly yellow oil and identified from its $^{31}P$, $^{13}C$, and $^1H$ NMR and the mass spectrum. $^{31}P\{^1H\}$ NMR ($CDCl_3$): δ 18.6 (s, PO), −4.1 (s, P); $^{13}C\{^1H\}$ NMR ($CDCl_3$): δ 140.6 (dd, $J_{CP}$=16.1, 3.1 Hz), 133.3 (dd, $J_{CP}$=19.9, 19.5 Hz), 131.5 (dd, $J_{CP}$=10.4, 9.5 Hz), 129.3 (d, $J_{CP}$=188.8 Hz), 62.0 (d, $J_{CP}$=5.4 Hz), 16.1 (d, $J_{CP}$=5.8 Hz); $^1H$ NMR ($CDCl_3$): δ 7.81 (m, 6H, $C_6H_4$), 7.40 (m, 6H, $C_6H_4$), 4.16 (m, 12H, $OCH_2$), 1.35 (m, 18H, $CH_3$); IR (neat film), $cm^{-1}$: 2986 (s), 2935 (m), 2909 (m), 1560 (s) 1479 (m), 1447 (m), 1405 (s), 1257 (vs), 1172 (s), 1140 (s), 1040 (vs, broad), 965 (vs, broad), 807 (s, broad), 743 (s); ESMS (positive ion mode): 671.1 $[M+H]^+$(100%).

Example 6

Preparation of Tris(4-phosphonophenyl)phosphine, hexasodium salt (II).

The procedure of example 2 was carried out using 21.25 g (92.39 mmol) of III, with the following modifications. After overnight evaporation of the ammonia, deoxygenated ether and water were added to the remaining organic phase. The aqueous phase was separated and sparged vigorously with nitrogen to remove volatile materials. The mixture was then acidified with deoxygenated hydrochloric acid to a pH of 1. This resulted in the formation of a viscous brown material. The mixture was heated and stirred vigorously under nitrogen until a yellow-brown suspension was obtained. The reaction mixture was filtered to give 4.80 g of a tan powder. Cooling the filtrate at 5° C. for 48 h gave another 5.49 g of an off-white powder, for a total recovery of 10.29 g (55% yield) of crude I. Compound I (5.38 g, ~0.011 mol) was taken up in ~15 mL of degassed methanol and a freshly prepared solution of 2.578 g NaOH in 2.6 mL degassed water was added dropwise. A thick suspension started to form, which separated to an oily second phase once the addition was complete. The solvent was removed using the rotary evaporator and the residue was triturated with acetone to give an off-white solid. Drying under oil-vacuum pump gave 7.49 g of material. The compound was purified by dissolving the solid in warm, deoxygenated water, filtering the solution under nitrogen through a plug of glass wool to remove a small amount of brown precipitate, and introducing the filtrate into a nitrogen-flushed vial. The solution was then layered with small amount of ethanol and allowed to cool slowly to room temperature. Colorless needles of II exhibiting marked efflorescence were obtained, precluding acquisition of satisfactory elemental analysis. Consequently, the identity of II was confirmed by single crystal x-ray diffraction. The purity was verified by $^{31}P\{^1H\}$, $^{13}C\{^1H\}$, and $^1H$ NMR analysis. Crystallography data: empirical formula $C_{18}H_{66}Na_6O_{36}P_4$; MW=1120.53; Z=6; space group=R3; unit cell dimensions: a=30.581(1) 0, b=30.581(1) 0, c=8.917(1) 0, α=90 °, β=90 °, γ=120 °; $^{31}P\{^1H\}$ NMR ($D_2O$): δ 11.4 (s, PO), −7.2 (s, P); $^1H$ NMR ($D_2O$): δ 7.74 (m, 6H, $C_6H_4$), 7.44 (m, 6H, $C_6H_4$); $^{13}C\{^1H\}$ NMR ($D_2O$): δ 144.5 (d, $J_{CP}$=268 Hz), 138.9 (d, $J_{CP}$=9.2 Hz), 135.6 (dd, $J_{CP}$=30.5, 9.5 Hz), 133.2 (apparent triplet; $J_{CP}$=13.1, 12.5 Hz); IR (KBr disk): 1878 $cm^1$(vs.), 1136 $cm^{-1}$(s), 1087 $cm^{-1}$(s), 1073 $cm^{-1}$ (s), 971 $cm^{-1}$ (s). ESMS (negative ion mode): 261.1 $[M-5Na+3H]^{2-}$(100%), 166.4 $M-6Na+3H]^{3-}$(40%).

Example 7

Preparation of Tris($^4$-phosphonophenyl)phosphine (I):

Crude compound I was prepared as described in example 6 and dissolved in the minimum amount of hot, deoxygenated water. The mixture was filtered to remove a small amount of brown precipitate. The clear, colorless filtrate was lyophilized to give I as a spectroscopically pure white powder. IR (KBr disc), cm$^{-1}$: 1590 (m), 1475 (w), 1383 (m), 1145 (vs, broad), 994 (vs, broad), 940 (vs, broad), 823 (s), 756 (m), 725 (w), 636 (w); ES-MS (negative ion mode): 501.3 [M–H]$^-$(100%), 752.1 [3M–2H]$^-$(34%), 1003.5 [2M–H]$^-$(18%). NMR data was obtained by neutralizing an analytical sample with NaOH in D$_2$O. $^{31}$P, $^{13}$C, and $^1$H NMR spectra were identical to II (example 6).

While presently preferred embodiments have been shown of the novel compounds and the process of preparation, persons skilled in this art will readily appreciate that various additional changes and modifications may be made without departing from the spirit of the invention as defined and differentiated by the following claims.

What is claimed is:

1. A compound and salts thereof, the compound having the following structural formula:

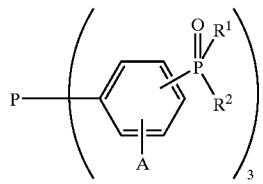

where R$^1$ and R$^2$ are selected from hydroxyl groups, dialkylamino groups, and alkoxide groups; and having at least one is A per phenyl ring which is stable to preparation reaction and does not interfere with solubility of the compound in the preparation reaction.

2. The compound of claim 1 wherein the phosphonate group is located at position 3 or 4 on each phenyl ring and A is selected from the group consisting of lower alkyl groups containing 1–6 carbon atoms, ether groups, phenol salt groups, dialkylamino groups, phenyl groups, lower alkyl phenyl groups, and mixtures thereof.

3. The compound of claim 1 wherein A is hydrogen.

4. The compound of claim 1 wherein R$^1$ and R$^2$ are selected from the group consisting of dialkylamino groups and alkoxide groups, and wherein the dialkylamino groups contain 1–22 carbon atoms and the alkoxide groups contain 1–22 carbon atoms.

5. The compound of claim 4 wherein the dialkylamino groups contain 1–6 carbon atoms and the alkoxide groups contain 1–6 carbon atoms.

6. The compound of claim 5 wherein where R$^1$ and R$^2$ are same and wherein the phosphonate group is located at position 3 or 4 on each phenyl ring.

7. The compound of claim 1 in which A is hydrogen; the single phosphonate group is a substituent at position 3 or 4 of each phenyl ring with R$^1$=R$^2$, wherein R$^1$ and R$^2$ are selected from the group consisting of —OH, —NMe$_2$, and —ONa.

8. A process comprising the steps of reacting phosphorus, an alkali metal, a proton donor and a fluorophenyl phosphonic acid derivative and recovering a compound defined by the following structural formula:

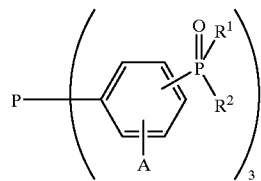

wherein the fluorophenyl phosphoric acid derivative is

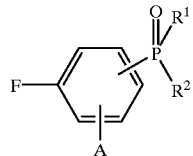

where in the above two formulas R$^1$ and R$^2$ are selected from dialkylamino groups and alkoxide groups; and having at least one A per phenyl ring which is stable to preparation reaction and does not interfere with solubility of the compound in the preparation reaction.

9. The process of claim 8 wherein the reaction is carried out in liquid ammonia and wherein the proton donor is t-butanol.

10. The process of claim 9 wherein the reaction is carried out in liquid ammonia-tetrahydrofuran mixture and wherein the proton donor is t-butanol.

11. The process of claim 9 wherein the reaction is carried out in one pot without isolation of any intermediates.

12. The process of claim 9 wherein the compound contains substituent A selected from the group consisting of lower alkyl groups containing 1–6 carbon atoms, ether groups, phenol salt groups, lower dilalkylamino groups, phenyl groups, lower alkylphenyl groups, and mixtures thereof.

13. The process of claim 9 wherein the compound is water soluble and the phosphonate group is located at position 2, 3 or 4.

14. The process of claim 9 wherein A is hydrogen.

15. The process of claim 9 wherein R$^1$ and R$^2$ are identical ethoxide groups or dimethylamino groups and the phosphonate group located at position 4 of the phenyl rings.

16. The process of claim 8 wherein the reaction is carried out in a solvent containing liquid ammonia; the proton donor is t-butanol; the alkali metal is lithium; R$^1$ and R$^2$ are same and are selected from the group consisting of OEt, NMe$_2$, groups and mixtures thereof.

17. The process of claim 8 wherein the molar ratio of phosphorus/alkali metal/proton donor is about 1:3:1.

18. The process of claim 17 including the step of hydrolyzing the compound to form a salt thereof.

19. The process of claim 18 wherein said step of hydrolyzing includes acid hydrolysis and optional treatment with a base.

* * * * *